United States Patent
Mickelsen

(10) Patent No.: US 12,178,503 B1
(45) Date of Patent: Dec. 31, 2024

(54) TISSUE ABLATION CATHETER WITH PASSIVE CONDUCTIVE ELEMENTS TO SHAPE ELECTRIC FIELDS

(71) Applicant: FIELD MEDICAL, INC., Cardiff By The Sea, CA (US)

(72) Inventor: Steven Mickelsen, Cardiff By The Sea, CA (US)

(73) Assignee: FIELD MEDICAL, INC., Cardiff By The Sea, CA (US)

( * ) Notice: Subject to any disclaimer, the term of this patent is extended or adjusted under 35 U.S.C. 154(b) by 0 days.

(21) Appl. No.: 18/824,027

(22) Filed: Sep. 4, 2024

Related U.S. Application Data

(63) Continuation-in-part of application No. 18/346,575, filed on Jul. 3, 2023, which is a continuation of application No. 18/078,795, filed on Dec. 9, 2022, now Pat. No. 11,690,671.

(51) Int. Cl.
*A61B 18/14* (2006.01)
*A61B 18/00* (2006.01)

(52) U.S. Cl.
CPC ...... *A61B 18/1492* (2013.01); *A61B 2018/00083* (2013.01); *A61B 2018/00577* (2013.01); *A61B 2018/00767* (2013.01)

(58) Field of Classification Search
CPC ...... A61B 18/1492; A61B 2018/00083; A61B 2018/00577; A61B 2018/00767
See application file for complete search history.

(56) References Cited

U.S. PATENT DOCUMENTS

| | | | |
|---|---|---|---|
| 6,102,046 A * | 8/2000 | Weinstein | A61B 18/148 606/41 |
| 11,259,869 B2 | 3/2022 | Mickelsen | |
| 2002/0049438 A1 * | 4/2002 | Sharkey | A61B 18/1402 604/35 |
| 2015/0182740 A1 * | 7/2015 | Mickelsen | A61M 25/0606 606/41 |

OTHER PUBLICATIONS

International Search Report and Written Opinion issued in PCT/US2023/083408 on Jan. 26, 2024.

* cited by examiner

*Primary Examiner* — Michael F Peffley
*Assistant Examiner* — Bo Ouyang
(74) *Attorney, Agent, or Firm* — ARC IP Law, PC; Joseph J. Mayo

(57) ABSTRACT

A catheter for tissue ablation with one or more inner electrodes inside the lumen, one or more outer electrodes attached to the outer surface, and one or more passive conductive elements that are not connected to the power supply but that passively shape the electrical field. The electrodes may be offset from the catheter's distal end. The material between the inner and outer electrodes may be an insulator such as a dielectric with a high dielectric constant. This catheter configuration generates an electric field that bends around the tip of the catheter. The number, position, shape, and size of passive conductive elements may affect the shape of the electric field to improve ablation effectiveness and consistency. The active electrodes or passive conductors may be coupled to the inner surface of the catheter body, or they may be located inside the lumen so that fluid flows around them during ablation.

18 Claims, 11 Drawing Sheets

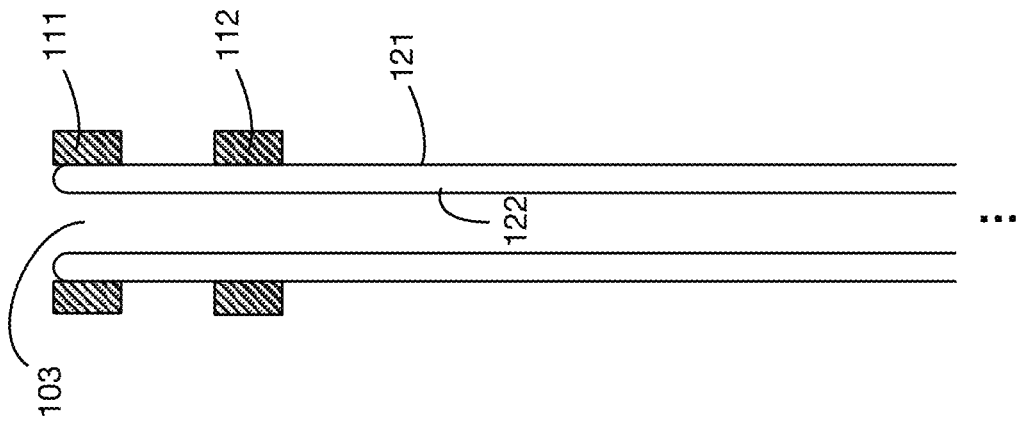
PRIOR ART
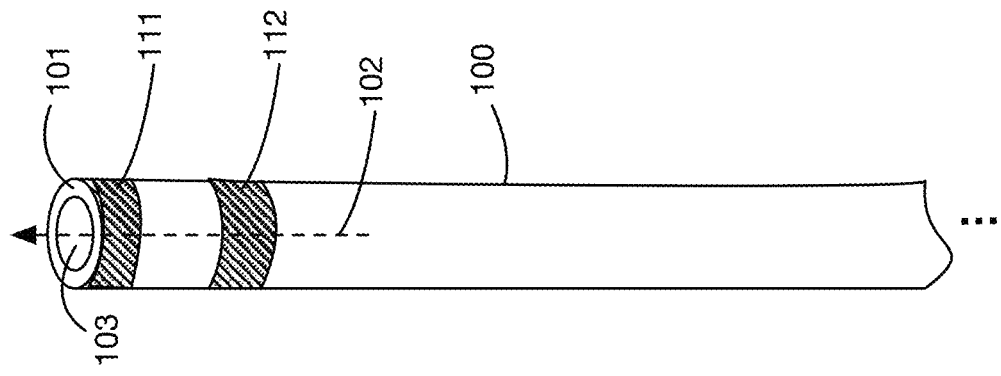

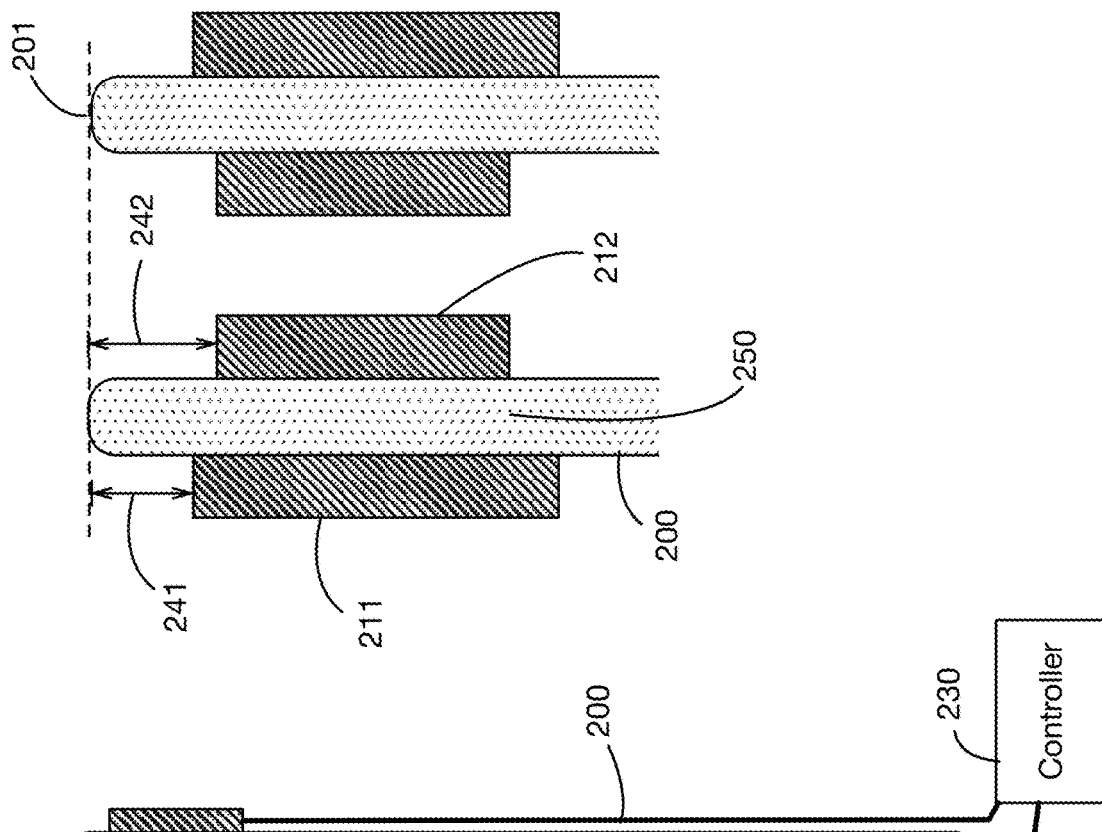
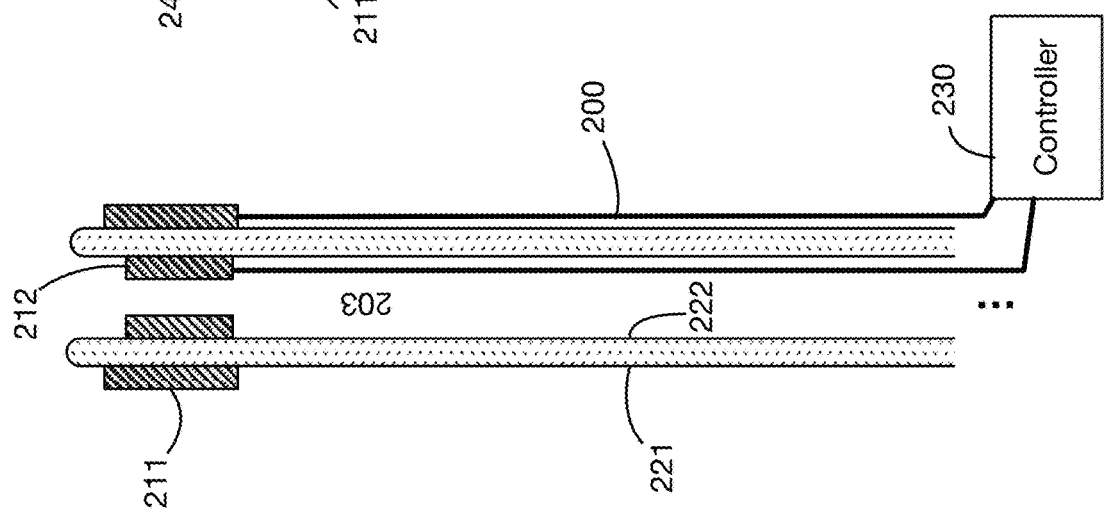
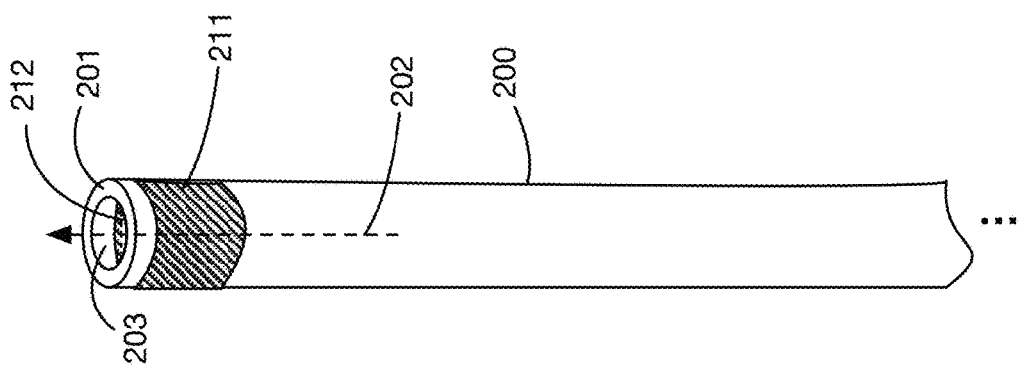

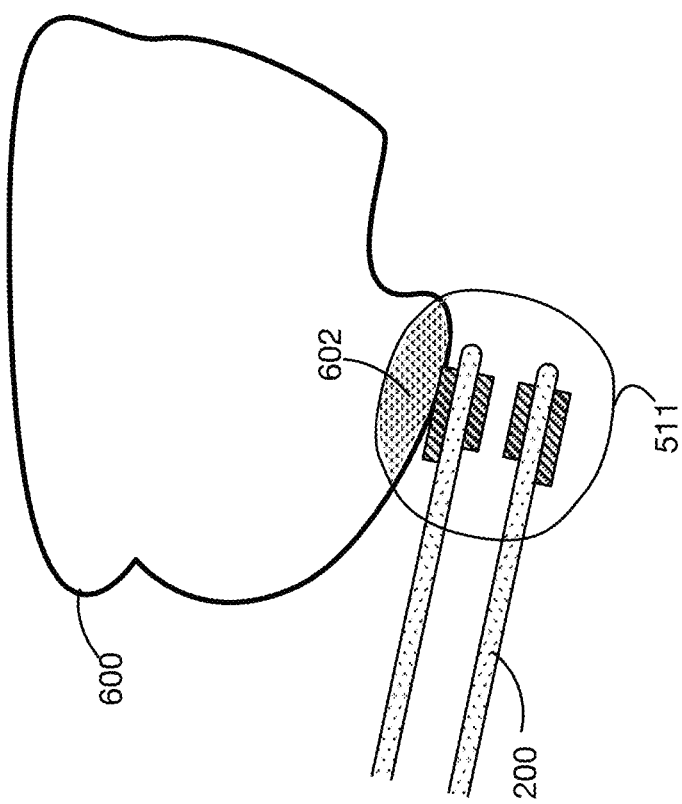
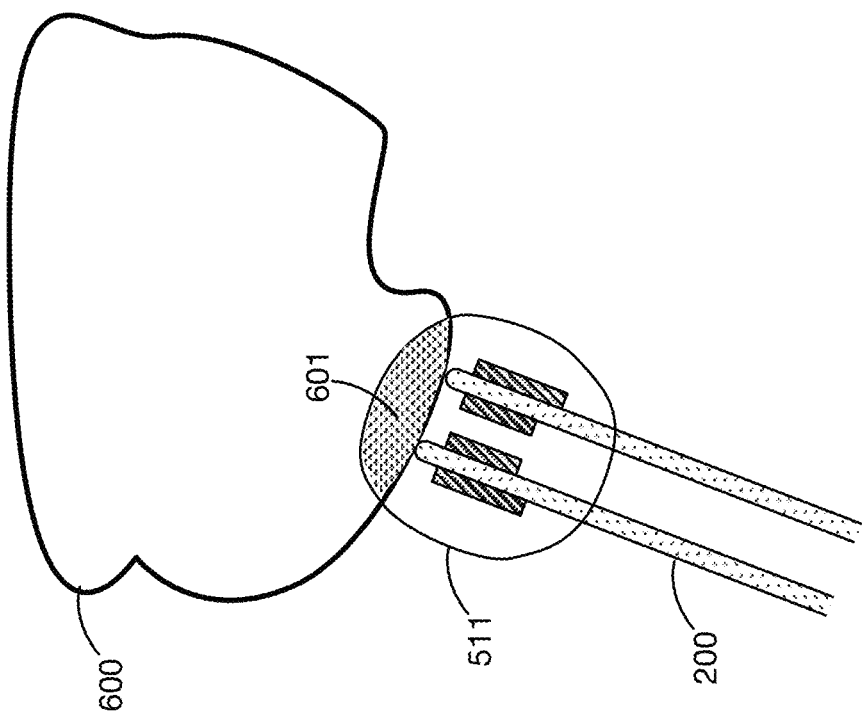

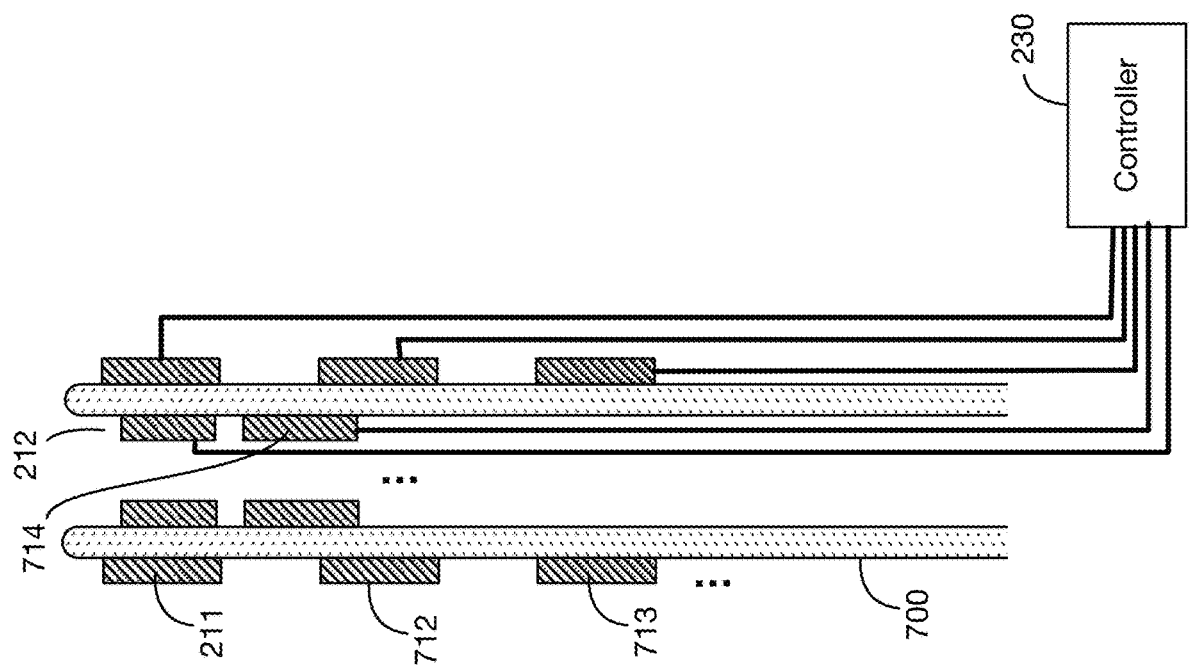

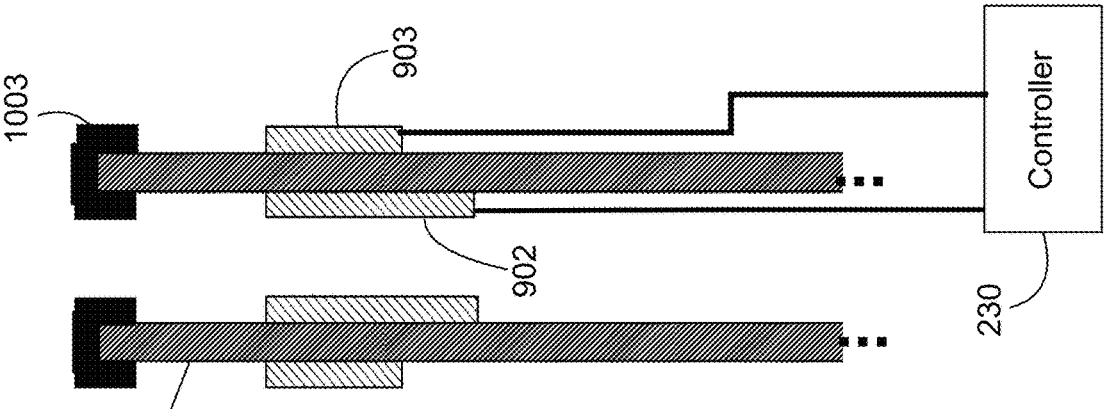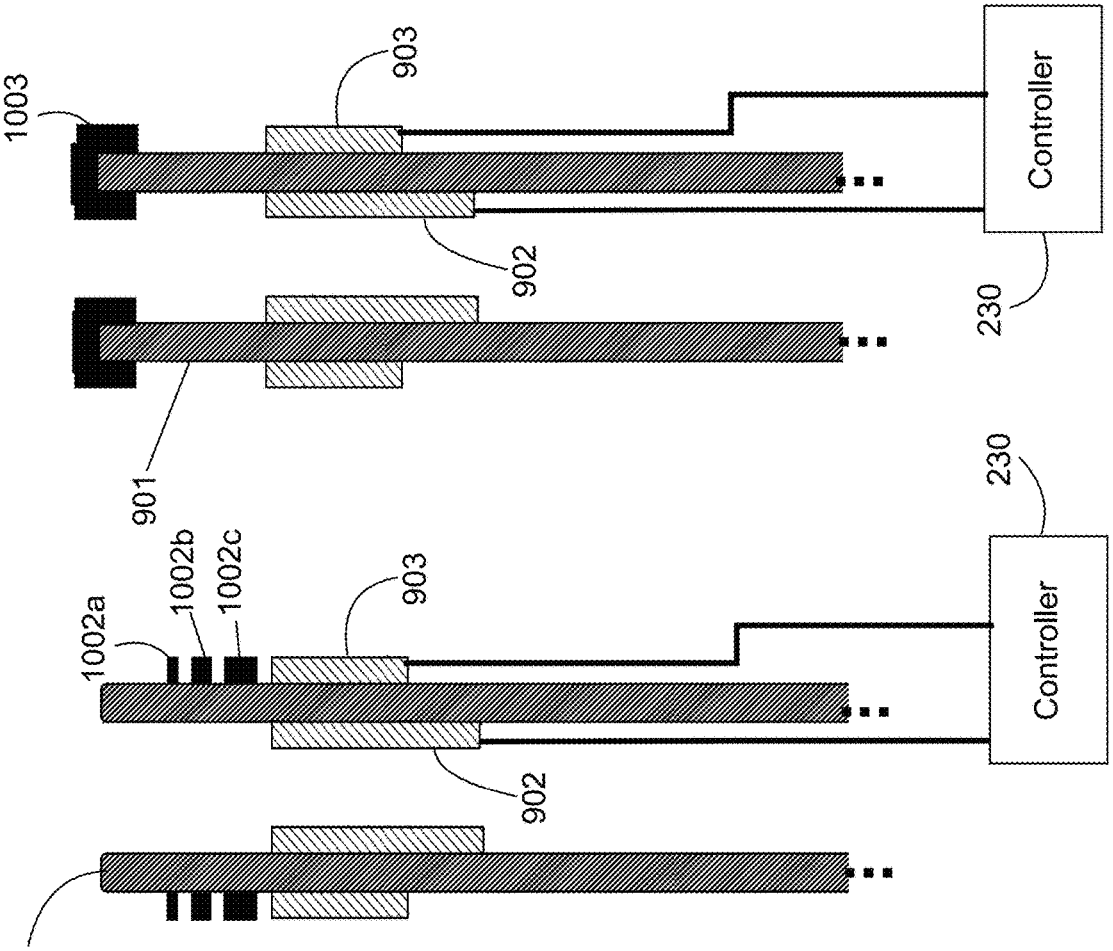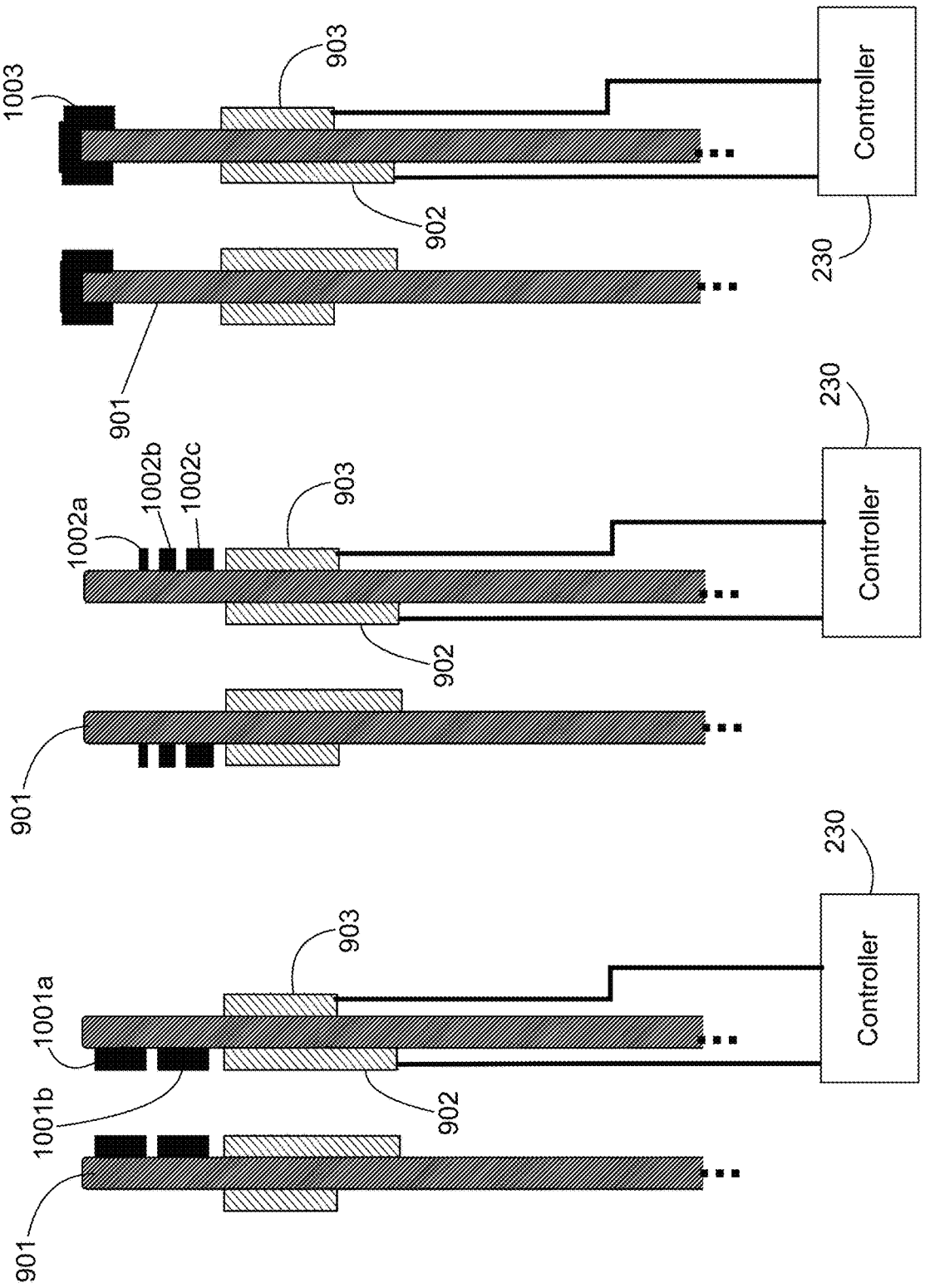

TISSUE ABLATION CATHETER WITH PASSIVE CONDUCTIVE ELEMENTS TO SHAPE ELECTRIC FIELDS

This application is a continuation-in-part of U.S. Utility patent application Ser. No. 18/346,575 filed 3 Jul. 2023, which is a continuation of U.S. Utility patent application Ser. No. 18/078,795 filed 9 Dec. 2022, the specifications of which are hereby incorporated herein by reference.

BACKGROUND OF THE INVENTION

Field of the Invention

One or more embodiments of the invention are related to the field of medical catheters used for tissue ablation. More particularly, but not by way of limitation, one or more embodiments of the invention enable a tissue ablation catheter with passive conductive elements to shape electric fields.

Description of the Related Art

Catheters with attached electrodes are widely used for tissue ablation to address a variety of medical issues. For example, for cardiac applications specialized multielectrode catheters have been invented to deliver electroporation to the ostium of pulmonary veins within the left atrium. Many of these devices are designed to perform anatomic ablation of the pulmonary veins to treat a common arrhythmia called atrial fibrillation.

Although existing ablation catheters have a wide variety of electrode configurations, they all place electrodes on the outer surface of the catheter, and typically have one electrode at the tip of the catheter. These configurations limit the shape of the electric fields that are generated by these catheters. In particular the electric field contours are typically elongated because they are generated by dipoles aligned with the longitudinal axis of the catheter. These elongated field shapes are not optimal for tissue ablation because ablation depth depends on the orientation of the catheter relative to the tissue to be ablated. The field shapes of existing catheters are also limited by the placement of the active electrodes; they do not use other elements such as passive conductive elements (conductors not connected to the power supply) to further shape the electric field for optimal ablation.

For at least the limitations described above there is a need for a tissue ablation catheter with passive conductive elements to shape electric fields.

BRIEF SUMMARY OF THE INVENTION

One or more embodiments described in the specification are related to a tissue ablation catheter with passive conductive elements to shape electric fields. Embodiments of the invention may generate novel electric field shapes that improve ablation consistency.

One or more embodiments of the invention may include a catheter with a tubular element having a longitudinal axis, a distal end, a lumen, an inner surface surrounding the lumen, and an outer surface. There may be an electrical insulator between the inner surface and the outer surface. The catheter may have one or more inner electrodes coupled to the inner surface, and one or more outer electrodes coupled to the outer surface. The inner electrodes and the outer electrodes may each be offset from the distal end of the catheter. The electrical insulator may separate the inner electrodes from the outer electrodes. The distal end of the catheter may be placed near a tissue to ablated. The controller may set the voltages of the inner and outer electrodes to generate an electric field outside the tubular element that induces ablation of the tissue by electroporation.

In one or more embodiments of the invention the shortest path of electrical current flowing from an inner electrode to an outer electrode may be longer than the distance between the inner and outer electrode.

In one or more embodiments of the invention the electrical insulator may be a dielectric, such as aluminum nitride ceramic for example. In one or more embodiments the conductivity of the electrical insulator may be less than 0.1 micro-Siemens per centimeter.

In one or more embodiments the distance between the distal end of the catheter tubular element and each of the inner electrodes may be greater than or equal to 0.01 millimeters and less than or equal to 1 meter. In one or more embodiments the distance between the distal end of the catheter tubular element and each of the outer electrodes may be greater than or equal to 0.01 millimeters and less than or equal to 1 meter.

In one or more embodiments of the invention the controller may set a magnitude of a potential difference between at least one inner electrode and at least one outer electrode of greater than 1000 volts. In one or more embodiments of the invention the controller may set a magnitude of a potential difference between at least one inner electrode and at least one outer electrode of greater than 5000 volts.

In one or more embodiments of the invention the controller may modify the voltages of the inner and outer electrodes within a pulse time that is less than two times the membrane recovery time of the tissue to be ablated.

In one or more embodiments the controller may modify the voltages of the inner and outer electrodes within a period that is less than or equal to 10 milliseconds.

In one or more embodiments the controller may modify voltages of the inner and outer electrodes to change the direction of the electric field outside the tubular element over time. For example, the controller may set electrode voltages at one time to generate a first average electric field vector in a region of the tissue to be ablated, and may set electrode voltages at another time to generate a second average electric field vector in a region of the tissue to be ablated, where the angular difference between the first and second average electric field vector is at least 1 degree.

In one or more embodiments, the catheter may also have one or more passive conductive elements coupled to the tubular element. Each passive conductive element may not be coupled to the controller, and it may have a conductive material such that charges within the conductive material move to modify the electric field.

In one or more embodiments, one or more of the passive conductive elements may be coupled to the inner surface and may be offset from the distal end in the proximal direction towards the proximal end.

In one or more embodiments, one or more of the passive conductive elements may be coupled to the outer surface.

In one or more embodiments, one or more of the passive conductive elements may be coupled to the distal end of the tubular element.

In one or more embodiments, at least one of the inner electrodes may be located in a position within the lumen where fluid flowing through the lumen flows around the edges of this inner electrode. In one or more embodiments, this inner electrode may have a shape that is cylindrical, spherical, or ellipsoidal.

In one or more embodiments, at least one of the passive conductive elements may be located in a position within the lumen where fluid flowing through the lumen flows around the edges of this passive conductive element. In one or more embodiments, this passive conductive element may have a shape that is cylindrical, spherical, or ellipsoidal.

BRIEF DESCRIPTION OF THE DRAWINGS

The above and other aspects, features and advantages of the invention will be more apparent from the following more particular description thereof, presented in conjunction with the following drawings wherein:

FIG. 1A shows a typical ablation catheter in the prior art, with electrodes on the outer surface of the catheter. FIG. 1B shows a cross-section view of the catheter of FIG. 1A.

FIG. 2A shows an illustrative embodiment of the invention, which is an ablation catheter with an outer electrode and an inner electrode. FIG. 2B shows a cross-section view of the catheter of FIG. 2A, and FIG. 2C shows a close-up cross-section view of the distal end of the catheter of FIG. 2A.

FIGS. 6A and 6B show a benefit of the symmetric field contour illustrated in FIG. 5B: tissue ablation depth is largely independent of the orientation of the catheter relative to the tissue to be ablated.

FIG. 7 shows a variation of the catheter of FIG. 2A with multiple inner electrodes and multiple outer electrodes.

FIG. 10A, FIG. 10B, and FIG. 10C shows variations of the catheter of FIG. 9B with one or more passive field-shaping conductive elements in different locations.

DETAILED DESCRIPTION OF THE INVENTION

Figure 3:
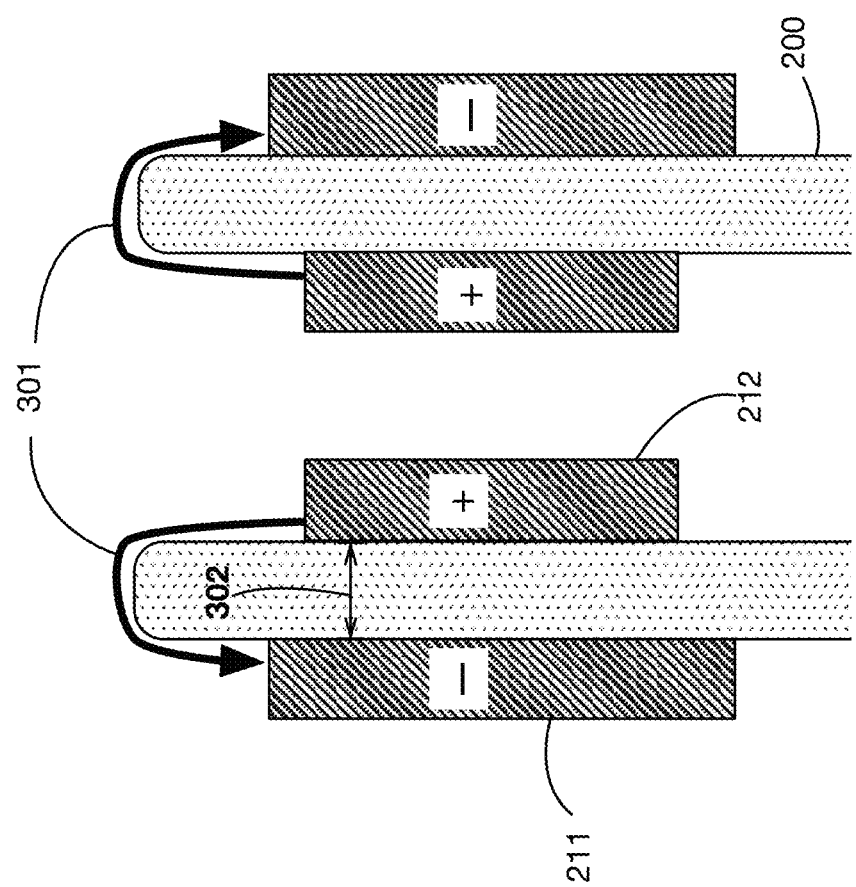
FIG. 3 shows an illustrative shortest current path between the inner and outer electrodes of the catheter of FIG. 2A; the current path is longer than the straight-line distance between the electrodes because the electrodes are separated by an insulator.

A tissue ablation catheter with passive conductive elements to shape electric fields will now be described. In the following exemplary description, numerous specific details are set forth in order to provide a more thorough understanding of embodiments of the invention. It will be apparent, however, to an artisan of ordinary skill that the present invention may be practiced without incorporating all aspects of the specific details described herein. In other instances, specific features, quantities, or measurements well known to those of ordinary skill in the art have not been described in detail so as not to obscure the invention. Readers should note that although examples of the invention are set forth herein, the claims, and the full scope of any equivalents, are what define the metes and bounds of the invention.

Intravascular catheters are used in medicine to deliver high voltage short duration pulsed electricity—also known as pulsed-field ablation, electroporation, DC ablation, fulguration—to tissue targets in a body for the purposes of soft tissue ablation. FIGS. 1A and 1B show a schematic of a typical ablation catheter 100 currently used for these applications. FIG. 1A shows a side view of an ablation catheter and FIG. 1B shows a cross section view along a plane through the catheter's longitudinal axis 102. Catheter 100 is a typical bipolar ablation catheter with a central lumen 103 inside a tubular element, and two electrodes on the outer surface 121 of the tube: electrode 111 is at or near the tip of the catheter at its distal end 101, and electrode 112 is located down the tube of the catheter away from the tip electrode. The electrodes are not attached to the inner surface 122. When a voltage difference is applied between the two electrodes, they form a dipole. Tissue may be ablated either with radiofrequency (RF) thermal energy or by electroporation where the electric field directly induces cell damage. Electric field mediated cell injury has advantages over thermal ablation and there has been a growing interest in technologies that use this approach over a range of medical conditions. Tissue response to electroporation is different than thermal injury in three important ways. First, tissue sensitivity to electric field mediated injury differs by orders of magnitude offering the advantage of selective ablation in some organs like the heart. Tissue selectivity can reduce risk of unintentional injury to collateral structures like phrenic nerve, esophagus, and blood vessels—common concerns when performing pulmonary vein isolation. Second, the size and shape of the lesion are more predictable and/or precise than thermal approaches because the ablation lesion volume closely follows the electric field contour. And third, electroporation is much faster than RF ablation ranging from microseconds to a few seconds for each application, reducing risks and resource requirements related to total procedural time.

Some ablation catheters have more than two electrodes on the outer surface 121 of the catheter 100. For cardiac applications for example, specialized multielectrode catheters have been invented to deliver electroporation to the ostium of pulmonary veins within the left atrium. Most of these devices are designed to perform anatomic ablation of the pulmonary veins to treat a common arrhythmia called atrial fibrillation.

FIGS. 2A, 2B, and 2C show different views of an illustrative embodiment of the invention, which is an ablation catheter 200 with novel geometric and electrical properties that offers advantages compared to a traditional ablation catheter such as catheter 100. FIG. 2A shows a side view of catheter 200; FIG. 2B shows a cross section view along a plane through the catheter's longitudinal axis 202; and FIG. 2C shows a closeup cross section view of the distal end of the catheter 200. Catheter 200 has an outer electrode 211 attached to the outer surface 221 of the tubular catheter body, and an inner electrode 212 attached to the inner surface 222 (facing the lumen 203) of the tubular catheter body. Both electrodes 211 and 212 are offset along the longitudinal axis 202 from the distal end 201 of the catheter; there is no electrode at the catheter tip. Distance 241 between the outer electrode 211 and the distal end 201 may be at least 0.01 millimeters and at most 1 meter in one or more embodiments of the invention. Similarly distance 242 between the inner electrode 212 and the distal end 201 may be at least 0.01 millimeters and at most 1 meter in one or more embodiments of the invention. The distances 241 and 242 may or may not be equal. In applications, the distal end of the catheter 200 may be placed at or near a tissue to be ablated. The outer electrode 211 may be in contact with the tissue. The inner electrode 212 is not in direct contact with the tissue to be ablated. The electrodes may generate an electric field outside the tubular catheter body that induces ablation of nearby tissue via electroporation. The lumen 203 of the catheter may carry an irrigation fluid that is infused into the tissue; this fluid may be conductive. An illustrative fluid may be 9% normal saline, for example.

Inner electrode 212 and inner electrode 211 are separated by the distal portion of the catheter body, which may contain an electrically insulating material 250. In one or more embodiments the conductivity of this insulating material 250 may be less than 0.1 micro-Siemens per centimeter, for example. In one or more embodiments this material 250 may be a dielectric and it may have a high dielectric constant. An illustrative material that may be used in one or more embodiments may be aluminum nitride ceramic for example. (The portion of the catheter body below the electrodes (away from the distal end) may or may not be made of the same material as the portion of the body between the electrodes.) All or a portion of the catheter body may be flexible. The tubular catheter body may be of any desired length.

Electrodes 211 and 212 may be coupled to a controller 230 that may set the voltage of each electrode, as shown in FIG. 2B. (The wires connecting the controller to the electrode are shown schematically as separated from the catheter body for ease of illustration; in applications these wires may be integrated into or attached to the catheter body, for example.) Controller 230 may deliver voltage pulses to the electrodes 211 and 212. The pulses may be for example monophasic pulses with a duration between 10 ns and 10 ms, <50% duty cycle, amplitude between 1 kV-30 kV, pulse repetition between 1 and 10,000 pulses/second, inclusive. In particular, in one or more embodiments of the invention the magnitude (absolute value) of the voltage applied between at least one inner electrode and at least one outer electrode may be greater than 1000 volts, and in one or more embodiments it may be greater than 5000 volts. However, any electric potential pattern could be used with this electrode configuration including but not limited to multiple duration rectangular pulses, biphasic rectangular or trapezoidal waves, sinusoidal bipolar, sinusoidal offset, asymmetric rectangular, asymmetric rectilinear, and/or any combination of arbitrary waveform or pulse pattern combination.

One or more embodiments of the invention may have more than one inner electrode or more than one outer electrode. FIG. 7 shows an illustrative embodiment with multiple inner and multiple outer electrodes. Embodiments may have any number of inner electrodes and any number of outer electrodes. The inner electrode(s) and outer electrode (s) may be separated by an insulator, such as a material with a high dielectric constant. All of the inner and outer electrodes may be offset from the distal end of the catheter.

FIG. 3 shows the effect of the geometry of catheter 200 on the flow of current between the electrodes. With the inner electrode set to a positive voltage relative to the outer electrode (for illustration), current 301 flows from inner electrode 212 along the lumen to the distal end of the catheter tip, and the bends and flows down to the outer electrode 211. (Inner and outer electrodes may be of any polarity; for example, in one or more embodiments, or at different times, an inner electrode may be negative, and an outer electrode may be positive. In this situation current 301 would flow in the opposite direction.) The length of the shortest current path 301 between the electrodes is therefore longer than the straight-line distance 302 between the electrodes. This feature is in contrast with the traditional catheter geometry of a catheter such as catheter 100 of FIG. 1A, where the length of the shortest current path between electrodes equals the straight-line distance between them, because the electrodes are not separated by an insulator between them.

Figure 4:
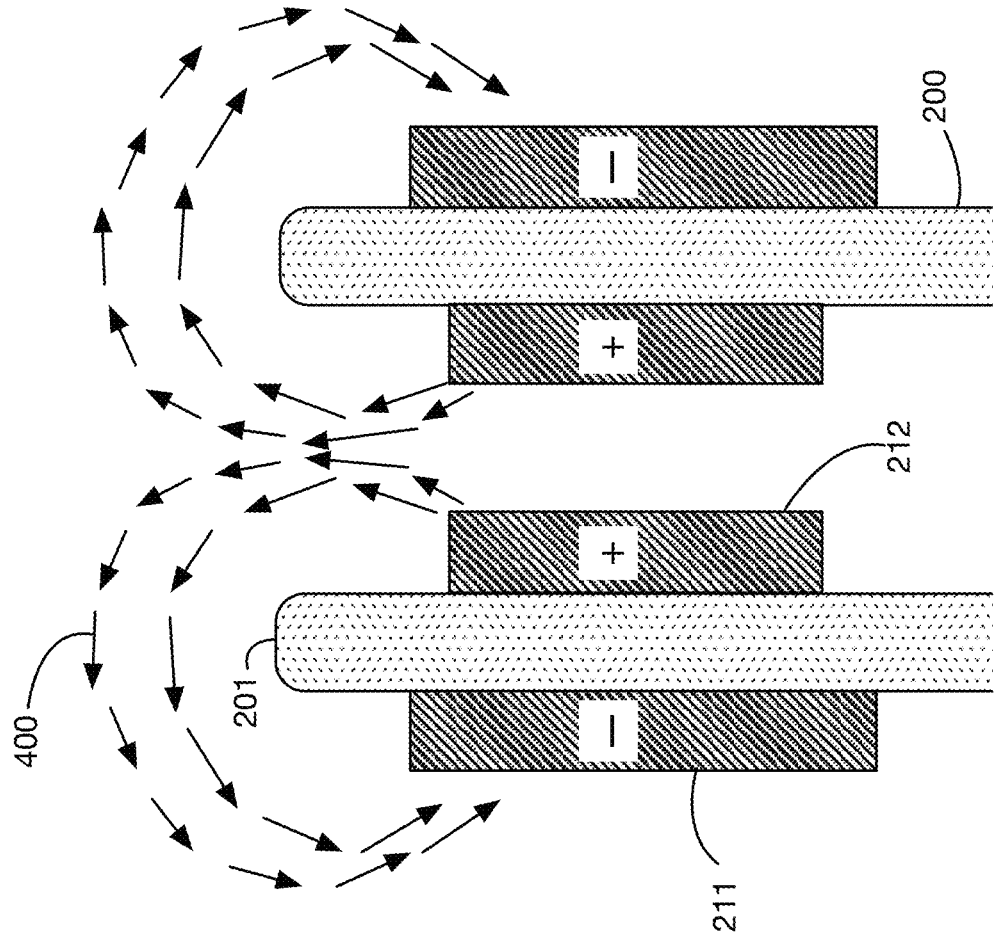
FIG. 4 shows illustrative electric field vectors in the region around the distal end of the catheter of FIG. 2A; the electric field bends around the insulator at the distal end between the inner and outer electrode.

FIG. 4 illustrates a similar bending effect on the shape of the electric field generated when a voltage difference is applied between the electrodes. The electric field lines 400 bend around the distal end of the catheter. The dielectric in the catheter body amplifies the field strength as it bends around the tip. (If inner electrode 212 were negative and outer electrode 211 were positive, electric field lines 400 would have the same shape but would point in the opposite directions.)

Figure 5B:
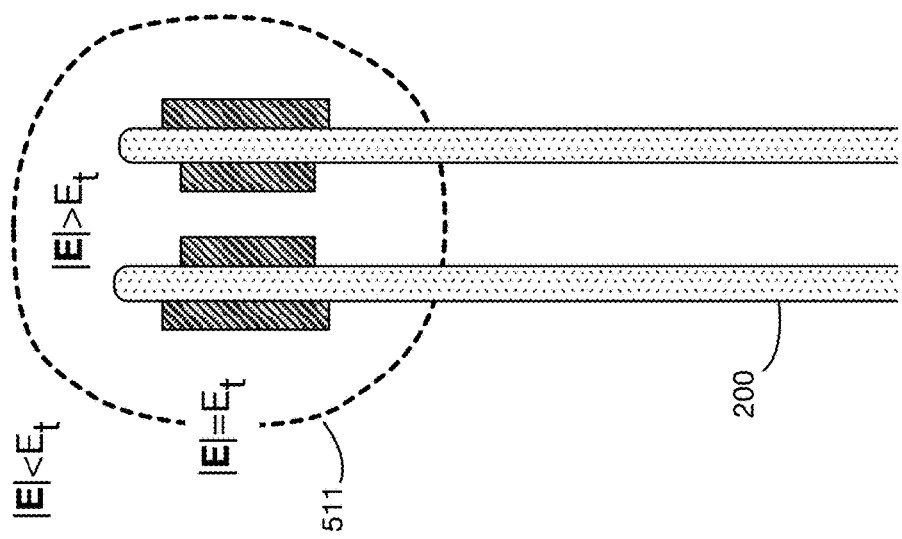
FIG. 5B shows this contour around the distal end of the catheter of FIG. 2A. The catheter of the invention has a more symmetric field contour than that of catheters in the prior art.
Figure 5A:
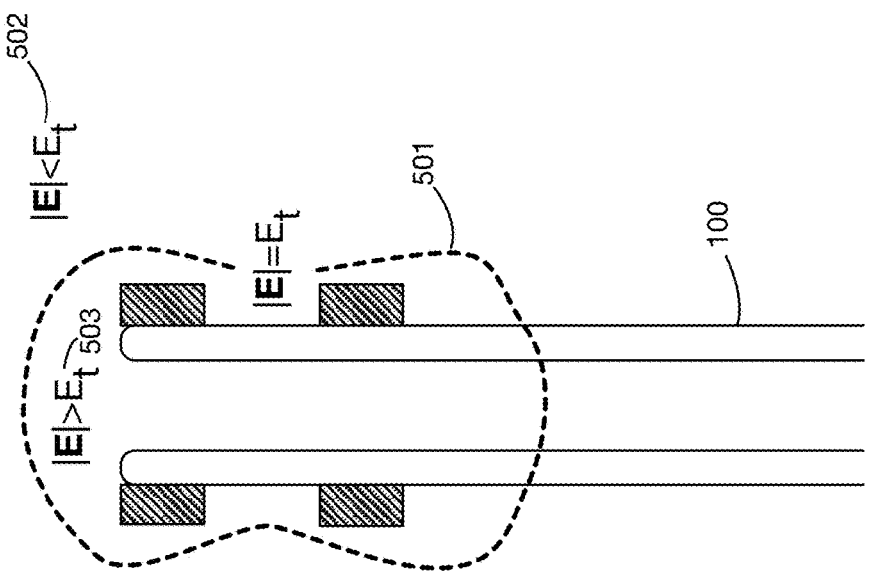
FIG. 5A shows an illustrative electric field strength contour around the distal end of the catheter of FIG. 1A.

FIGS. 5A and 5B illustrate a potential benefit of the bent electric field line shape shown in FIG. 4 compared to the field shape from a traditional ablation catheter. FIG. 5A shows an electric field strength contour 501 for traditional catheter 100, and FIG. 5B shows a similar contour 511 for catheter 200. The contour lines 501 and 511 separate regions within the contours where the field strength is above a threshold value from regions outside the contours where the field strength is below this threshold value. Because tissue ablation via electroporation is highly correlated with electric field strength, the shape of the field strength contours determines the regions where tissue will be ablated. Because the electrodes in catheter 100 operate in a traditional dipole configuration, the contour 501 is elongated; in contrast, because of the field bending phenomenon, the contour 511 is relatively symmetrical around the tip of catheter 200. This symmetric shape provides a consistent depth of tissue ablation regardless of the orientation of the catheter relative to the tissue to be ablated. This benefit is illustrated in FIGS. 6A and 6B. Catheter 200 is placed against tissue 600, with the objective of ablating a portion of the tissue near the catheter. However, it is not always possible to control the precise orientation of the catheter relative to the tissue. For example, in FIG. 6A, the longitudinal axis of the catheter 200 is approximately perpendicular to the tissue boundary, while in FIG. 6B this axis is approximately parallel to the tissue boundary. Because the electrical field strength contour 511 is substantially symmetric, the portion of tissue 601 that experiences a field strength greater than the threshold value when the catheter is perpendicular is almost identical to the portion of tissue 602 that experiences this field strength when the catheter is parallel. Thus, the depth of tissue ablated will be approximately the same regardless of the catheter orientation. This feature of catheter 200 represents a substantial advance over traditional catheters with highly asymmetrical field strength contours, for which ablation depth may be highly dependent on catheter orientation that cannot necessarily be controlled.

Catheter 200 has a single inner electrode and a single outer electrode. One or more embodiments of the invention may have multiple inner or multiple outer electrodes (or both). FIG. 7 shows illustrative catheter 700 with two inner electrodes 212 and 714, and three outer electrodes 211, 712, and 713. All electrodes are offset from the distal end of the catheter, and inner and outer electrodes are separated by the insulating catheter body. All of the electrodes are coupled to controller 230. The controller may set the voltages of any of the electrodes and may vary these voltages over time to change the direction and strength of the electric field vectors. By varying the electrode voltages, the target tissue may be exposed to multiple electric field vectors from a single catheter position. (A change in the polarity of one or more electrodes is considered to be a particular type of change in voltage, since the sign of the voltage changes relative to other electrodes when polarity is reversed. Voltage changes of electrodes therefore encompass polarity changes, even if voltage magnitudes are unchanged when polarities are reversed. A voltage change may change either or both of the magnitude or sign of an electrode's voltage relative to any other electrode or relative to a ground.)

Figure 8C:
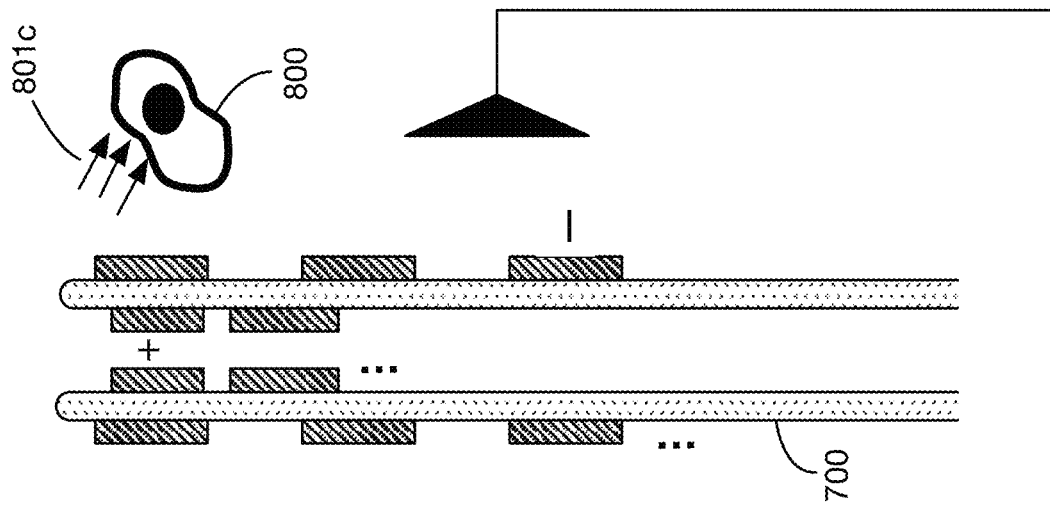
FIGS. 8A, 8B, and 8C show how the direction of the electric field acting on a cell of the tissue to be ablated can be modified by altering the voltages in the electrodes of the catheter of FIG. 7.
Figure 8B:
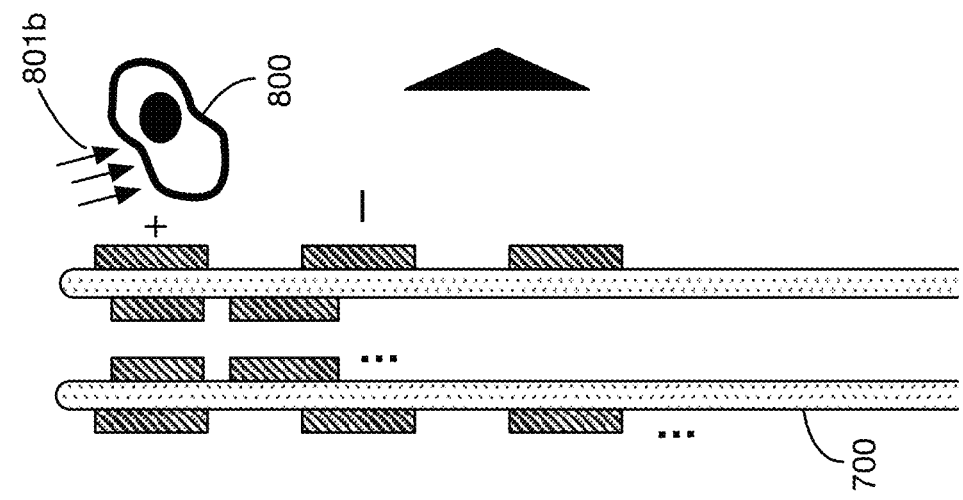
Figure 8A:
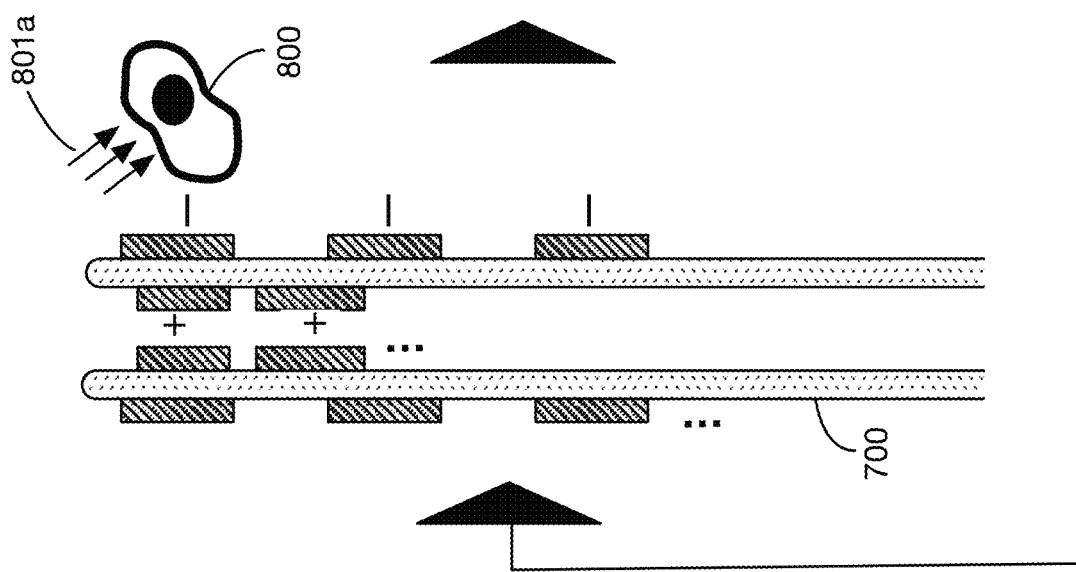

FIGS. 8A, 8B, and 8C show an embodiment that modifies electrode voltages to change electric field vector directions over time. The effect of an electric field on tissue ablation depends on both the field strength and on the orientation of the field vector relative to cell membranes. Generally, the greatest stress on cells occurs where the electric field vector is perpendicular to the cell membrane. However, cell membranes are oriented heterogeneously throughout tissue, so a single field direction does not generate maximum stress on all cells simultaneously. By subjecting tissue to multiple field directions over time, the ablation of cells within the tissue will be more uniform since each cell will experience field vectors that are more likely to provide high stress on that cell's membrane. FIGS. 8A through 8C show different voltage patterns applied to the electrodes of catheter 700 at different times, and the resulting average field directions 801a through 801c near an illustrative cell 800 in the target tissue. The controller may for example repeatedly cycle among these three voltage patterns. Modifying the voltages exposes the cell to different field directions at different times. For example, a volume sample within the target tissue may be exposed to two or more average electric field vectors at different times that differ by a calculated vector angle difference between 1° to 90°, inclusive. In one or more embodiments the switching time between different voltage configurations may be less than or equal to twice the membrane recovery time of target cell or material within the treatment volume. For example, the switching time between configurations may be between 10 ns and 1 second.

In addition to the catheter features described above that shape the directions and strengths of electric field lines, one or more embodiments of the invention may add one or more "passive conductive elements" to an ablation catheter to further shape the electrical field. Passive field-shaping conductive elements may be conductors (made of any conductive material) that are not connected to the catheter's power source. They may be placed anywhere on the catheter, including inside or outside the lumen. Because these passive conductive elements are conductors, they modify the shape of an electrical field generated by the active electrodes, since free charges within the conductors migrate in response to the external electric field from the active electrodes.

Figure 9C:
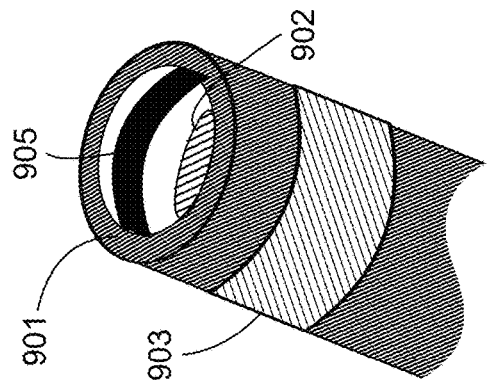
FIG. 9C shows an oblique view of the catheter of FIG. 9B.
Figure 9B:
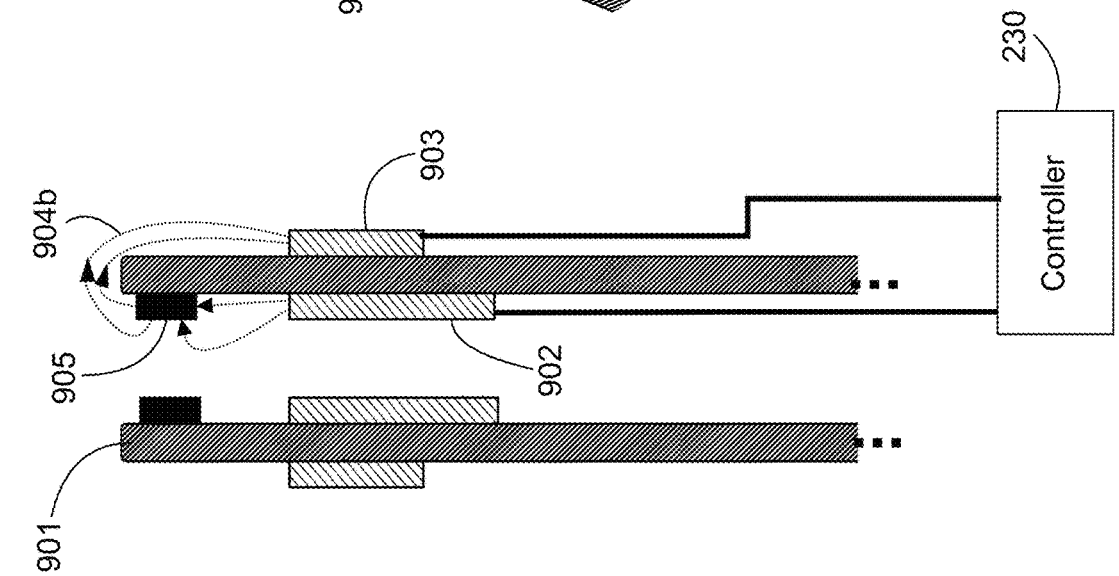
FIG. 9B shows the effect on these field lines of adding a passive conductive element (a conductor not connected to the power source) to the catheter.
Figure 9A:
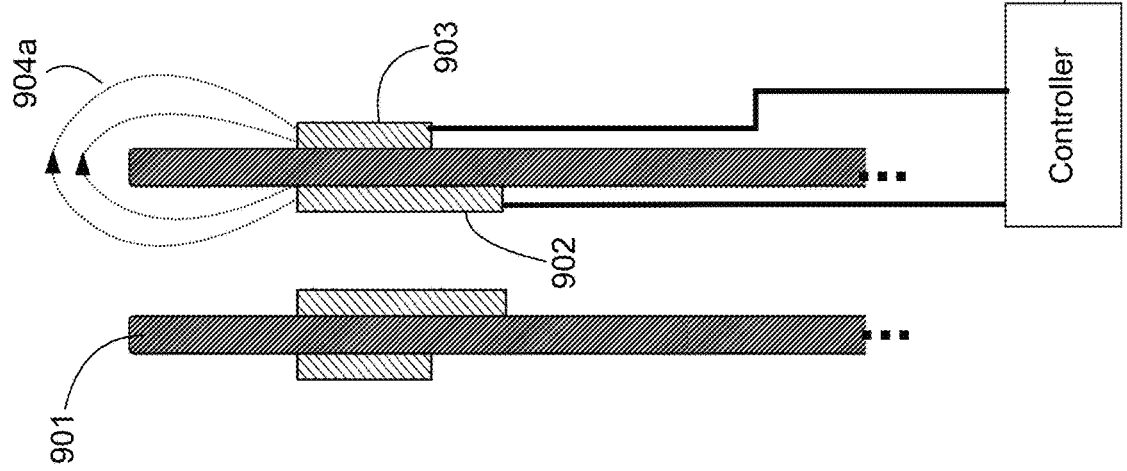
FIG. 9A shows illustrative electric field lines for a catheter like the one shown in FIG. 4.

FIG. 9A shows a cross-section view (along the longitudinal axis) of a catheter 901 similar to the ones described above for example in FIG. 4. This catheter has an internal electrode 902, and an external electrode 903. The electrodes may be annular, for example, with the inner electrode along the inner wall of the catheter tube, and the outer electrode along the outer wall of the catheter tube. Both are coupled electrically to controller 230, which may set and modify voltages applied to the two electrodes to generate an electric field between them. All or part of the tube between the two electrodes may be an insulator. FIG. 9A shows illustrative electric field lines 904a between electrodes 902 and 903.

FIG. 9B shows catheter 901 of FIG. 9A with a passive field-shaping conductive element 905 (shown in black) added near the tip of the catheter, slightly recessed from the tip, and on the inner wall of the lumen. Passive field-shaping conductive element 905 may be made of or may contain any conductive material or materials. Passive field-shaping conductive element 905 is not connected to controller 230; it does not receive power or voltage from any power source; it simply reacts passively to an applied external electrical field generated for example by the active electrodes 902 and 903. The passive conductive element 905 influences the shape of the electric field lines; the illustrative field lines 904b with the passive conductive element are closer to the tip of the catheter in this example than the field lines 904a without the passive field-shaping conductive element. One or more embodiments of the invention may use any number of passive conductive elements, in any locations and of any shapes and sizes, to modify the shape of the electric field (and thus of the flow of current) as desired.

FIG. 9C shows an oblique view of the top of catheter of FIG. 9B. The catheter tube body 901 may be made for example of an insulator. Inner electrode 902 (only partially visible within the lumen) is annular and is situated on the inner wall of the lumen. Outer electrode 903 is also annular and it surrounds the outer wall of the catheter body. Passive field-shaping conductive element 905 is also annular (and also only partially visible) and is on the inside of the catheter, above active electrode 902 but below the catheter tip. All of the positions of these active and passive conductive elements are illustrative; one or more embodiments may position active and passive conductive elements in any locations.

FIGS. 10A, 10B, and 10C show illustrative variations on the number, sizes, and locations of passive field-shaping conductive elements. In the embodiment shown in FIG. 10A, there are two annular passive field-shaping conductive elements 1001a and 1001b located inside the catheter body, offset vertically from each other and from active inner electrode 902, and offset from the tip of the catheter. In the embodiment of FIG. 10B, there are three passive field-shaping conductive elements 1002a, 1002b, and 1002c that surround the outer wall of the catheter body 901; all are located between the active outer electrode 903 and the catheter tip, offset from the tip. These passive conductive elements are all annular, and they are of different sizes with 1002a the smallest and 1002c the largest. In the embodiment of FIG. 10C, a single annular passive field-shaping conductive element 1003 is placed around the tip of the catheter.

Figure 11B:
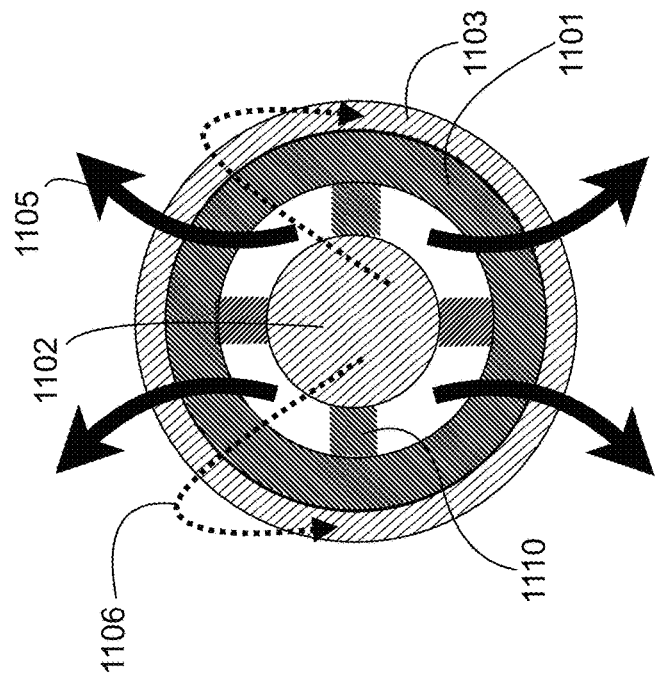
FIG. 11B shows a top view of the catheter of FIG. 11A.
Figure 11A:
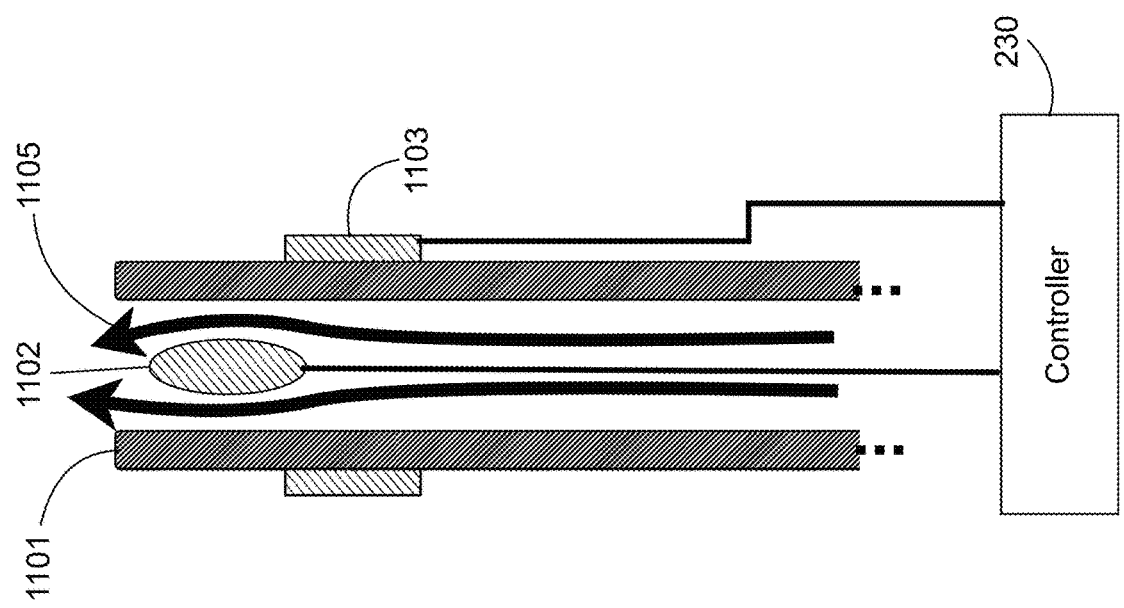
FIG. 11A shows a vertical cross-section view of a variation of a catheter like the one shown in FIG. 9A, where the inner electrode is within the lumen of the catheter in a position that allows fluid to flow around the electrode.

In many of the illustrative embodiments described above, active electrodes may be attached to (or integrated into) either the outer wall or the inner wall of the catheter tube body. In one or more embodiments of the invention, one or more inner electrodes may be located inside the lumen, and irrigation fluid flowing through the lumen may flow around the edges of the inner electrode. This configuration may have benefits for example in heat transfer between the fluid and the inner electrode(s), and it may affect the shape of the electrical field, for example by making the source of field lines at or near the center of the catheter lumen. FIG. 11A shows a cross section view (along the longitudinal axis of the catheter) of an illustrative embodiment with an annular outer electrode 1103, and an inner electrode 1102 situated within the lumen. The inner electrode is not directly attached to the inner wall of catheter tube body 1101. Fluid 1105 that flows through the lumen passes around the inner electrode 1102. Inner electrode 1102 may have for example a cylindrical, spherical, or ellipsoidal shape. It may be recessed from the catheter tip, or in one or more embodiments it may extend from the catheter tip. It may or may not be symmetrical around the longitudinal axis of the lumen. In one or more embodiments, fluid may flow only around some of the sides of the inner electrode 1102. One or more embodiments may have multiple inner electrodes that are located within the lumen but not attached to the inner catheter wall. One or more embodiments may have a mixture of inner electrodes attached to the inner wall and inner electrodes located within the lumen so that fluid flows around them.

Because an inner electrode surrounded by fluid typically needs some support so that it stays in position, in one or more embodiments of the invention such an electrode may be supported by material that is coupled to or that extends from the inner wall of the lumen. This approach is illustrated in FIG. 11B, which shows a top view of the catheter of FIG. 11A. Inner electrode 1102 is supported by four struts, such as strut 1110, that extend from the inner wall of the catheter tube. Fluid 1105 flows between the struts and around the inner electrode 1102. Electric field lines such as field line 1106 flow between inner electrode 1102 and outer electrode 1103.

In one or more embodiments of the invention, one or more passive field-shaping conductive elements may also be located inside the catheter tube in a position wherein fluid flows around the passive field-shaping conductive elements. Any number of inner elements, either passive conductive elements or active electrodes, may be located wherein fluid flows around all or part of these elements.

While the invention herein disclosed has been described by means of specific embodiments and applications thereof, numerous modifications and variations could be made thereto by those skilled in the art without departing from the scope of the invention set forth in the claims.

What is claimed is:

1. A tissue ablation catheter with passive conductive elements to shape electric fields, comprising:
    a tubular element comprising:
        a distal end configured to be placed proximal to a tissue to be ablated;
        a proximal end opposite said distal end;
        an inner surface surrounding a lumen;
        an outer surface; and,
        an electrical insulator between said inner surface and said outer surface;
    one or more inner electrodes within said lumen, each offset away from said distal end in a proximal direction towards said proximal end;
    one or more outer electrodes coupled to said outer surface;
    a controller coupled to said one or more inner electrodes and to said one or more outer electrodes and configured to:
        set voltages of said one or more inner electrodes and voltages of said one or more outer electrodes to generate an electric field outside said tubular element that induces ablation of said tissue to be ablated by electroporation; and,
    one or more passive conductive elements coupled to said tubular element, wherein:
        each passive conductive element of said one or more passive conductive elements is not coupled to said controller; and each passive conductive element comprises a conductive material, wherein charges within said conductive material move to modify said electric field.

2. The tissue ablation catheter with passive conductive elements to shape electric fields of claim 1, wherein one or more of said one or more passive conductive elements are coupled to said inner surface and are offset away from said distal end in said proximal direction towards said proximal end.

3. The tissue ablation catheter with passive conductive elements to shape electric fields of claim 1, wherein one or more of said one or more passive conductive elements are coupled to said outer surface.

4. The tissue ablation catheter with passive conductive elements to shape electric fields of claim 1, wherein one or more of said one or more passive conductive elements are coupled to said distal end of said tubular element.

5. The tissue ablation catheter with passive conductive elements to shape electric fields of claim 1, wherein said controller is further configured to:
    modify the voltages of said one or more inner electrodes and said one or more outer electrodes over time to change a direction of said electric field outside said tubular element over time.

6. The tissue ablation catheter with passive conductive elements to shape electric fields of claim 5, wherein said controller is further configured to:
    set first voltages of said one or more inner electrodes and said one or more outer electrodes at a first time to generate a first average electric field vector in a region of said tissue to be ablated;
    set second voltages of said one or more inner electrodes and said one or more outer electrodes at a second time to generate a second average electric field vector in a second region of said tissue to be ablated;
    wherein an angular difference between said first average electric field vector and said second average electric field vector is at least 1 degree.

7. The tissue ablation catheter with passive conductive elements to shape electric fields of claim 5, wherein:
    said controller is further configured to modify said voltages of said one or more inner electrodes and said one or more outer electrodes within a pulse time that is less than two times a membrane recovery time of said tissue to be ablated.

8. The tissue ablation catheter with passive conductive elements to shape electric fields of claim 5, wherein:
    said controller is further configured to modify said voltages of said one or more inner electrodes and said one or more outer electrodes within a period that is less than or equal to 10 milliseconds.

9. The tissue ablation catheter with passive conductive elements to shape electric fields of claim 1, wherein a shortest path of electrical current flowing from an inner electrode of said one or more inner electrodes to an outer electrode of said one or more outer electrodes is longer than a distance between said inner electrode and said outer electrode.

10. The tissue ablation catheter with passive conductive elements to shape electric fields of claim 1, wherein said electrical insulator comprises a dielectric.

11. The tissue ablation catheter with passive conductive elements to shape electric fields of claim 10, wherein said dielectric comprises aluminum nitride ceramic.

12. The tissue ablation catheter with passive conductive elements to shape electric fields of claim 1, wherein conductivity of said electrical insulator is less than 0.1 microSiemens per centimeter.

13. The tissue ablation catheter with passive conductive elements to shape electric fields of claim 1, wherein said controller is further configured to set a magnitude of a potential difference between at least one of said one or more inner electrodes and at least one of said one or more outer electrodes to greater than 1000 volts.

14. The tissue ablation catheter with passive conductive elements to shape electric fields of claim 1, wherein said controller is further configured to set a magnitude of a potential difference between at least one of said one or more inner electrodes and at least one of said one or more outer electrodes to greater than 5000 volts.

15. The tissue ablation catheter with passive conductive elements to shape electric fields of claim 1, wherein:

at least one inner electrode of said one or more inner electrodes is located in a position within said lumen wherein fluid flowing through said lumen flows around edges of said at least one inner electrode.

16. The tissue ablation catheter with passive conductive elements to shape electric fields of claim 15, wherein said at least one inner electrode has a shape that is cylindrical, spherical, or ellipsoidal.

17. The tissue ablation catheter with passive conductive elements to shape electric fields of claim 1, wherein at least one passive conductive element of said one or more passive conductive elements is located in a position within said lumen wherein fluid flowing through said lumen flows around edges of said at least one passive conductive element.

18. The tissue ablation catheter with passive conductive elements to shape electric fields of claim 17, wherein said at least one passive conductive element has a shape that is cylindrical, spherical, or ellipsoidal.

* * * * *